(12) United States Patent
Kannan et al.

(10) Patent No.: US 9,131,899 B2
(45) Date of Patent: Sep. 15, 2015

(54) EFFICIENT HANDLING OF MISALIGNED LOADS AND STORES

(75) Inventors: Hari S. Kannan, Sunnyvale, CA (US); Pradeep Kanapathipillai, Santa Clara, CA (US); Greg M. Hess, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 845 days.

(21) Appl. No.: 13/177,192

(22) Filed: Jul. 6, 2011

(65) Prior Publication Data

US 2013/0013862 A1    Jan. 10, 2013

(51) Int. Cl.
| G06F 12/00 | (2006.01) |
| A61B 5/00 | (2006.01) |
| A61B 5/053 | (2006.01) |
| A61N 1/05 | (2006.01) |
| A61N 1/362 | (2006.01) |
| G06F 12/08 | (2006.01) |

(52) U.S. Cl.
CPC .............. *A61B 5/686* (2013.01); *A61B 5/0538* (2013.01); *A61B 5/4836* (2013.01); *A61B 5/7275* (2013.01); *A61N 1/05* (2013.01); *A61N 1/362* (2013.01); *G06F 12/0862* (2013.01); *G06F 12/0877* (2013.01); *G06F 12/0802* (2013.01)

(58) Field of Classification Search
None
See application file for complete search history.

(56) References Cited

U.S. PATENT DOCUMENTS

| 4,075,686 | A | 2/1978 | Calle et al. |
| 5,349,651 | A | 9/1994 | Hetherington et al. |
| 7,287,140 | B1 | 10/2007 | Asanovic et al. |
| 7,519,813 | B1 | 4/2009 | Cox et al. |
| 7,996,632 | B1 * | 8/2011 | Grohoski et al. ............. 711/154 |
| 2005/0080953 | A1 * | 4/2005 | Oner et al. ................... 710/52 |
| 2007/0050592 | A1 * | 3/2007 | Gschwind et al. ............ 711/201 |
| 2008/0010433 | A1 * | 1/2008 | Fluhr et al. ................... 711/206 |
| 2010/0262781 | A1 * | 10/2010 | Hrusecky et al. ............. 711/119 |

* cited by examiner

*Primary Examiner* — Cheng-Yuan Tseng
*Assistant Examiner* — Arvind Talukdar
(74) *Attorney, Agent, or Firm* — Rory D. Rankin; Meyertons, Hood, Kivlin, Kowert & Goetzel, P.C.

(57) ABSTRACT

A system and method for efficiently handling misaligned memory accesses within a processor. A processor comprises a load-store unit (LSU) with a banked data cache (d-cache) and a banked store queue. The processor generates a first address corresponding to a memory access instruction identifying a first cache line. The processor determines the memory access is misaligned which crosses over a cache line boundary. The processor generates a second address identifying a second cache line logically adjacent to the first cache line. If the instruction is a load instruction, the LSU simultaneously accesses the d-cache and store queue with the first and the second addresses. If there are two hits, the data from the two cache lines are simultaneously read out. If the access is a store instruction, the LSU separates associated write data into two subsets and simultaneously stores these subsets in separate cache lines in separate banks of the store queue.

19 Claims, 9 Drawing Sheets

EFFICIENT HANDLING OF MISALIGNED LOADS AND STORES

BACKGROUND OF THE INVENTION

1. Field of the Invention

This invention relates to computing systems, and more particularly, to efficiently handling memory misaligned accesses within a processor.

2. Description of the Relevant Art

Modern microprocessors are typically coupled to one or more levels of a cache hierarchy in order to reduce the latency of the microprocessor's request for data in memory. The request may result from a read or a write operation during the execution of one or more software applications. Generally, a cache may store multiple cache lines, where a cache line holds several bytes of data in contiguous memory locations. A cache line may be treated as a unit for coherency purposes. In addition, a cache line may be a unit of allocation and deallocation in the cache. By having a unit of allocation and deallocation of several bytes in a cache, memory accesses may be more efficient and have a smaller latency than having a unit of one or a few bytes.

Generally speaking, a read or a write operation that accesses a chunk of data smaller than a cache line and included within the cache line may not have an additional access penalty. The entire cache line is accessed during the operation regardless of the smaller size. For example, a cache line may have a size of 64 bytes. Whether an accessed 4-byte data chunk begins at an offset of 0 or an offset of 50 does not alter the access time. However, if the accessed data chunk is not aligned within the cache line boundaries (i.e., crosses a cache line boundary), then extra work may need to be performed.

For example, if an accessed 16-byte data chunk of a 64-byte cache line has an offset of 56, then one portion of the data is included in one cache line and the remainder is included in another cache line. In such a case, the processor performs two read operations to obtain the two successive cache lines instead of a single cache line read operation for the single load instruction. The processor may also perform at least an additional third operation to align the requested data, such as one or more rotate operations and join operations.

The extra processing described above may greatly increase the latency of a read or a write operation, which in turn reduces system performance. In some cases, misaligned memory requests are handled with micro-code support. The micro-code sequences each cache line, where sequencing refers to accessing a second cache line behind a first cache line. Sequencing, in addition to later rotation operations, adds considerable latency and code density. Further still, when a memory misalignment is detected for a load instruction, the processor pipeline may need to be flushed to allow the micro-code to properly handle the misalignment. The pipeline flush further reduces system performance.

In view of the above, efficient methods and mechanisms for handling misaligned memory accesses within a processor are desired.

SUMMARY OF EMBODIMENTS OF THE INVENTION

Systems and methods for efficiently handling misaligned memory accesses within a processor are contemplated. In one embodiment, a processor includes a load-store unit (LSU) with a banked data cache (d-cache) and a banked store queue. Each of the d-cache and the store queue may have an even bank and an odd bank based on an index portion of an address corresponding to a memory access instruction. The processor generates a first address corresponding to a received memory access instruction identifying a first cache line. The processor may determine the received memory access instruction is misaligned by crossing over a cache line boundary. In response to this determination, the processor may generate a second address corresponding to the memory access instruction identifying a second cache line logically adjacent to the first cache line. The LSU may access at least the d-cache simultaneously with both the first address and the second address.

In response to further determining the misaligned instruction is a load instruction and detecting a hit in the d-cache for each of the first address and the second address, the LSU may simultaneously read data from a first cache line and a second cache line corresponding to the first address and the second address, respectively. No additional accesses of the d-cache are performed despite the memory access exceeding the cache line boundary. Then the LSU may generate requested data corresponding to the load instruction by concatenating associated data read out from the first cache line and the second cache line. One or more rotation operations may be performed to align the requested data. In addition to accessing the banked d-cache, the LSU may simultaneously access the banked store queue. If the LSU detects a hit in the store queue for each of the first address and the second address, the LSU may simultaneously read data from a first entry corresponding to a first cache line and a second entry corresponding to a second cache line. Again, these two cache lines may correspond to the first address and the second address, respectively.

In response to further determining the misaligned instruction is a store instruction and detecting a hit in the banked store queue for each of the first address and the second address, the LSU may separate write data corresponding to the store instruction into a first subset and a second subset. The first and second subsets may correspond to the even bank and the odd bank, respectively, or vice-versa. Then the LSU may store each of the first subset and the second subset in a separate cache line in the even bank and the odd bank, respectively. A second access of the store queue is not performed to complete the write operation for the store instruction. The lack of one or more additional accesses of the d-cache and the store queue for misaligned memory accesses reduces latency and accordingly increases system performance.

These and other embodiments will be further appreciated upon reference to the following description and drawings.

Figure 1:
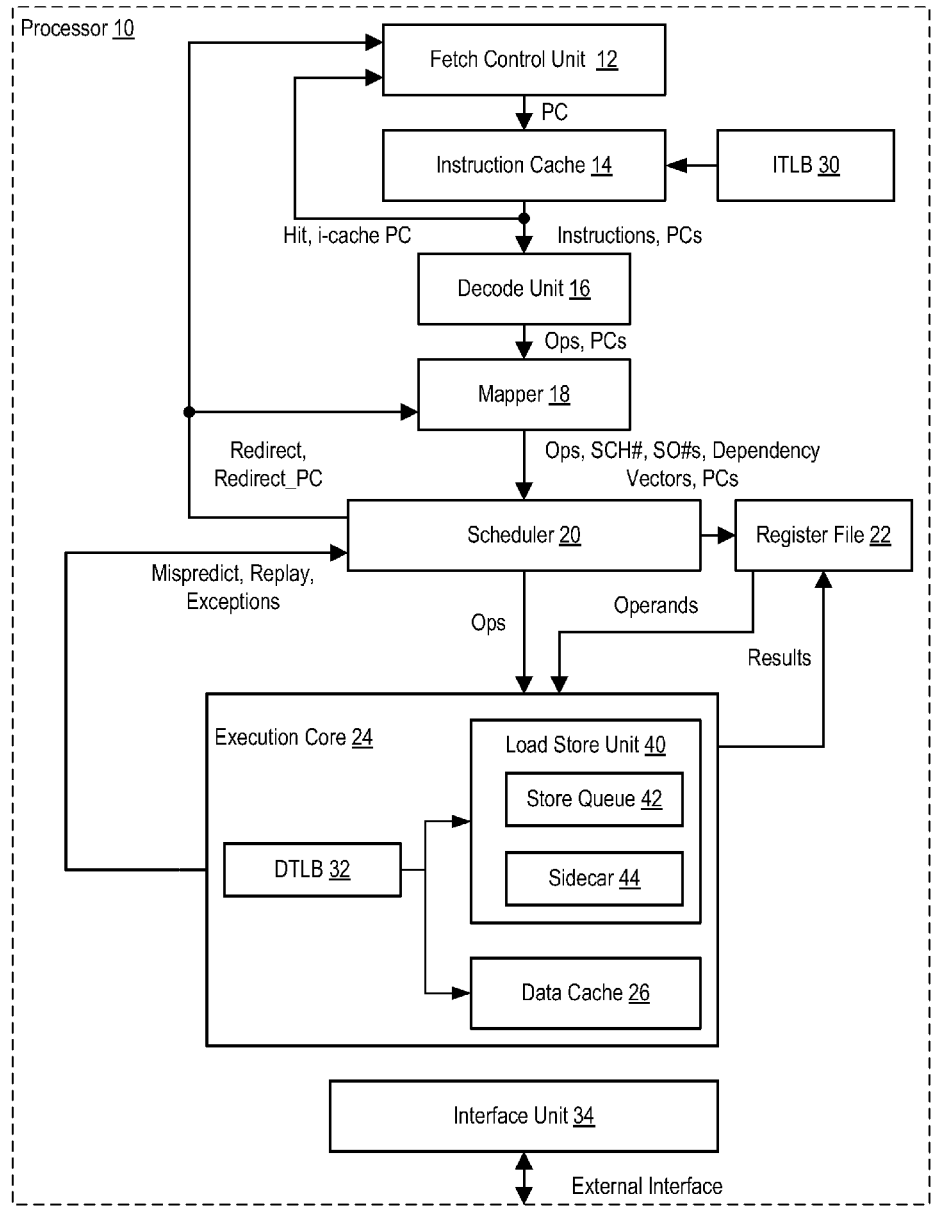
FIG. 1 is a generalized block diagram of one embodiment of a processor.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims. As used throughout this application, the word "may" is used in a permissive sense (i.e., meaning having the potential to), rather than the mandatory sense (i.e., meaning must). Similarly, the words "include," "including," and "includes" mean including, but not limited to.

Various units, circuits, or other components may be described as "configured to" perform a task or tasks. In such contexts, "configured to" is a broad recitation of structure generally meaning "having circuitry that" performs the task or tasks during operation. As such, the unit/circuit/component can be configured to perform the task even when the unit/circuit/component is not currently on. In general, the circuitry that forms the structure corresponding to "configured to" may include hardware circuits. Similarly, various units/circuits/components may be described as performing a task or tasks, for convenience in the description. Such descriptions should be interpreted as including the phrase "configured to." Reciting a unit/circuit/component that is configured to perform one or more tasks is expressly intended not to invoke 35 U.S.C. §112, paragraph six interpretation for that unit/circuit/component.

DETAILED DESCRIPTION OF EMBODIMENTS

In the following description, numerous specific details are set forth to provide a thorough understanding of the present invention. However, one having ordinary skill in the art should recognize that the invention might be practiced without these specific details. In some instances, well-known circuits, structures, and techniques have not been shown in detail to avoid obscuring the present invention.

Referring to FIG. 1, a generalized block diagram illustrating one embodiment of a processor 10 is shown. In the illustrated embodiment, the processor 10 includes a fetch control unit 12, an instruction cache 14, a decode unit 16, a mapper 18, a scheduler 20, a register file 22, an execution core 24, and an interface unit 34. As is well known in the art, the processor 10 may operate on multiple threads and include multiple cores, where each core includes the components shown in FIG. 1. A brief description of each of these components is provided here. A description of the execution core 24 including a load-store unit (LSU) 40 and a data cache 26 used for handling memory accesses is initially described. A description of the remaining components shown in processor 10 follows this description.

Generally, a cache may store one or more lines, each of which is a copy of data stored at a corresponding address in the system memory. As used herein, a "line" is a set of bytes stored in contiguous memory locations, which are treated as a unit for coherency purposes. As used herein, the terms "cache block", "block", "cache line", and "line" are interchangeable. In some embodiments, a cache line may also be the unit of allocation and deallocation in a cache. In some embodiments, each of the caches 14 and 26 may return one or more additional cache lines not yet requested when returning a first cache line that is requested. The instructions or data returned from this prefetch mechanism may be buffered for subsequent use.

In some embodiments, processor 10 may implement an address translation scheme in which one or more virtual address spaces are made visible to executing software. Memory accesses within the virtual address space are translated to a physical address space corresponding to the actual physical memory available to the system, for example using a set of page tables, segments, or other virtual memory translation schemes. In embodiments that employ address translation, the instruction cache 14 may be partially or completely addressed using physical address bits rather than virtual address bits. For example, instruction cache 14 may use virtual address bits for cache indexing and physical address bits for cache tags.

In order to avoid the cost of performing a full memory translation when performing a cache access, processor 10 may store a set of recent and/or frequently used virtual-to-physical address translations in a translation lookaside buffer (TLB), such as Instruction TLB (ITLB) 30. During operation, ITLB 30 (which may be implemented as a cache, as a content addressable memory (CAM), or using any other suitable circuit structure) may receive virtual address information and determine whether a valid translation is present. If so, ITLB 30 may provide the corresponding physical address bits to instruction cache 14. If not, ITLB 30 may cause the translation to be determined, for example by raising a virtual memory exception.

The execution core 24 may include several computation units that perform arithmetic operations, bitwise logic operations, and detection of branch mispredictions, The execution core 24 may calculate and compare target addresses for branch operations, and generate addresses for memory access operations. These computation units are not shown for ease of illustration. The execution core 24 may include a data cache 26, which may be a cache memory for storing data to be processed by the processor 10. A data TLB (DTLB) 32 may be provided to cache virtual-to-physical address translations for use in accessing the data cache 26 in a manner similar to that described above with respect to ITLB 30. It is noted that although ITLB 30 and DTLB 32 may perform similar functions, in various embodiments they may be implemented differently. For example, they may store different numbers of translations and/or different translation information.

The execution core 24 may include a load-store unit (LSU) 40 for processing memory access operations, such as integer and floating-point load and store instructions and other types of memory reference instructions. The LSU 40 may access the d-cache 26 and include logic for detecting data cache misses and to responsively request data from a cache hierarchy. For example, a miss request may go to a lower-level cache, such as at least a L2 data cache (not shown). In one embodiment, the d-cache 26 is a set-associative, write-through cache in which all stores are written to an L2 cache regardless of whether they hit in the d-cache 26. The actual computation of addresses for load/store instructions may take place within a computation unit in the execution core 24, though in other embodiments, the LSU 40 may implement dedicated address generation logic. In some embodiments, the LSU 40 may implement an adaptive, history-dependent hardware prefetcher configured to predict and prefetch data that is likely to be used in the future.

The LSU 40 may include load and store buffers configured to store issued but not-yet-committed load and store instructions for the purposes of coherency snooping and dependency checking for bypassing data. A store queue 42 may hold addresses of not-yet-committed store instructions. The data corresponding to these addresses may be stored in a separate store buffer (not shown). The store queue 42 and other load and store buffers maintain information for in-flight load and store instructions. A load instruction may have corresponding data from an older store instruction bypassed to it. The corresponding data may be stored in a store buffer prior to being written into the d-cache 26. As load instructions enter the LSU 40, a dependency check may be performed for determining possible data bypass.

The LSU 40 may include a miss buffer (not shown) configured to store outstanding loads and stores that cannot yet complete, for example due to cache misses. In addition, the LSU 40 may include a "sidecar" buffer 44 for storing a subset of requested data corresponding to an outstanding load instruction that is a misaligned memory access. The requested data for the load instruction may cross a cache line boundary and cause a misaligned access. Therefore, the requested data may be in a first subset in a first cache line and in a second subset in a second cache line. The first cache line may be stored in the store queue 42, the d-cache 26 or both. The second cache line may not be stored in either the store queue 42 or the d-cache 26, thus, causing a miss.

Continuing with the above example, the data held in the first subset of the first cache line that resulted in an access hit may be stored in the sidecar buffer 44. A miss request may be sent to the memory subsystem (cache hierarchy and DRAM) for the data stored in the second cache line. At a later time, when the miss request is serviced, the data held in the second subset that is returned from the memory subsystem may be joined with the data held in the first subset stored in the sidecar buffer 44. The combination of the first subset and the second subset may be used to complete the original load instruction. As used herein, a load instruction may be referred to as a read operation. Additionally, a store instruction may be referred to as a write operation. In combination with completing the load instruction with the data in each of the first subset and the second subset, the data stored in the returned second cache line may be placed in the d-cache 26.

The number of bytes in a cache line is conventionally a number based on the power of two. Therefore, alignment detection may utilize both the least-significant bits of a generated address corresponding to a memory access instruction and a size of the data to be accessed. If (i) the size of the access data is less than a size of a cache line and (ii) the size of allocation from the offset within the generated address to the end of the cache line is not able to fit the requested data, then the memory access instruction is misaligned and crosses a cache line boundary.

A misaligned memory access operation that crosses a cache line boundary typically accesses a location that does not begin at the beginning of an associated cache line. A second access, which does not currently occupy an additional issue slot in the processor adjacent to the current memory access operation, is performed to complete the original memory access operation. This additional access and subsequent stitching together of the requested data may be performed by micro-code in software or replay generated micro-operations in the hardware. However, each of these solutions increases latency and code density. An alternative solution may include structuring each of the d-cache 26 and the store queue 42 to have banks For example, an even bank and an odd bank may be used. The index portion of a generated address may be used to access one of these banks. Additionally, an incremented index based on the generated index portion may simultaneously access the other bank of these banks. Therefore, a subset of data within each of two cache lines may be simultaneously read out and placed on a data bus with a size of a single cache line. A further description is provided later below.

Continuing with a description of a misaligned memory access that crosses a cache line boundary, an example may include a load instruction that has a requested data size of 16 bytes and an offset of 56. This offset is a nonzero value. For a 64-byte cache line, the first 8 bytes of the requested data are located in bytes 56 to 63 of a first cache line identified by a generated first address corresponding to the load instruction. The latter 8 bytes of the requested data are located in bytes 0 to 7 of a second cache line logically adjacent to the first cache line. The second cache line may be identified by a generated second address that has an index with a value of an index within the first address incremented by one. For example, the first address may have a 10-bit tag value of 0x036, a 48-bit index value of 0x7777 DDDD 2264, and a 6-bit offset value of 0x38, where "0x" denotes a hexadecimal number representation. Therefore, the second address may have a same 10-bit tag value of 0x036, an incremented 48-bit index value of 0x7777 DDDD 2265, and a different 6-bit byte offset of 0x00.

Still continuing with the above example, the index portion with a value of 0x7777 DDDD 2264 may be used to access an even bank within each of the d-cache 26 and the store queue 42. The execution core 24, the LSU 40 and/or the d-cache 26, may generate a second index portion with a value of 0x7777 DDDD 2265. This second index portion may be used to simultaneously access an odd bank within each of the d-cache 26 and the store queue 42. If a tag hit occurs for each of the index portions, then a first subset located in bytes 56 to 63 of the first cache line in the odd bank identified by the first index portion is read out and placed on a result data bus. Simultaneously, a second subset located in bytes 0 to 7 of the second cache line in the even bank identified by the second index portion is read out and placed on a result data bus. Both the first subset and the second subset are simultaneously placed on the result data bus, which has a size of a single cache line. The placement of these subsets may follow a given format, such as being placed at the beginning of the data bus. The first subset may be placed in front of the second subset to create the 16-byte requested data.

One cause of cache memory misalignment may include hard drive write requests that write a data chunk that is not aligned with a size of the internal blocks of the hard drive. A second cause of misalignment may arise when optimizing code with multimedia extensions to an instruction set architecture (ISA), such as Streaming Single Instruction Multiple Data (SIMD) Extensions 2 (SSE2) from Intel Corp. An SSE2 algorithm often includes loading and storing data 16 bytes at a time to match the size of the XMM registers.

The execution core 24 may also be configured to detect various events during execution of ops that may be reported to the scheduler. Branch ops may be mispredicted, and some load/store ops may be replayed (e.g. for address-based conflicts of data being written/read). Various exceptions may be detected (e.g. protection exceptions for memory accesses or for privileged instructions being executed in non-privileged mode, exceptions for no address translation, etc.). The exceptions may cause a corresponding exception handling routine to be executed.

A further description of the remaining components in processor 10 now follows. The fetch control unit 12 is coupled to provide a program counter address (PC) for fetching from the instruction cache 14. The instruction cache 14 is coupled to provide instructions (with PCs) to the decode unit 16, which is coupled to provide decoded instruction operations (ops, again with PCs) to the mapper 18. Relatively simple op generations (e.g. one or two ops per instruction) may be handled in hardware while more extensive op generations (e.g. more than three ops for an instruction) may be handled in microcode. In addition, the fetch control unit 12 may handle branch prediction algorithms.

The mapper 18 is coupled to provide ops, a scheduler number (SCH#), source operand numbers (SO#s), one or more dependency vectors, and PCs to the scheduler 20. The mapper 18 may implement register renaming to map source register addresses from the ops to the source operand numbers (SO#s) identifying the renamed source registers. Additionally, the mapper 18 may be configured to assign a scheduler entry to store each op, identified by the SCH#. In one embodiment, the SCH# may also be configured to identify the rename register assigned to the destination of the op. In other embodiments, the mapper 18 may be configured to assign a separate destination register number. The mapper 18 may be configured to generate dependency vectors for the op. The dependency vectors may identify the ops on which a given op is dependent. The mapper 18 may provide the ops, along with SCH#, SO#s, PCs, and dependency vectors for each op to the scheduler 20.

The scheduler 20 is coupled to receive replay, mispredict, and exception indications from the execution core 24. In addition, the scheduler 20 may be coupled to provide a redirect indication and redirect PC to the fetch control unit 12 and the mapper 18, provide ops for execution to the execution core 24 and is coupled to the register file 22. The register file 22 is coupled to provide operands to the execution core 24, and is coupled to receive results to be written from the execution core 24. The register file 22 may generally include any set of registers usable to store operands and results of ops executed in the processor 10. In other embodiments, processor 10 may utilize reservation stations as part of a scheduling mechanism. For example, reservation stations may be utilized on a per execution unit basis. These and other embodiments are possible and are contemplated.

The execution core 24 is coupled to the interface unit 34, which is further coupled to an external interface of the processor 10. The external interface may include any type of interconnect (e.g. bus, packet, etc.). The external interface may be an on-chip interconnect, if the processor 10 is integrated with one or more other components (e.g. a system on a chip configuration). The external interface may be on off-chip interconnect to external circuitry, if the processor 10 is not integrated with other components. It is contemplated that processor 10 may implement any suitable instruction set architecture (ISA), such as, e.g., the ARM™, PowerPC™, or x86 ISAs, or combinations thereof.

The instruction cache 14 may be a cache memory for storing instructions to be executed by the processor 10. As described above, the data cache (d-cache) 26 may be a cache memory for storing user data used during processing of program instructions. Each of the instruction cache 14 and d-cache 26 may have any capacity and construction (e.g. direct mapped, set associative, fully associative, etc.). Each of the caches 14 and 26 may have any cache line size. For example, 64 byte cache lines may be implemented in an embodiment. Other embodiments may use larger or smaller cache line sizes.

Figure 2:
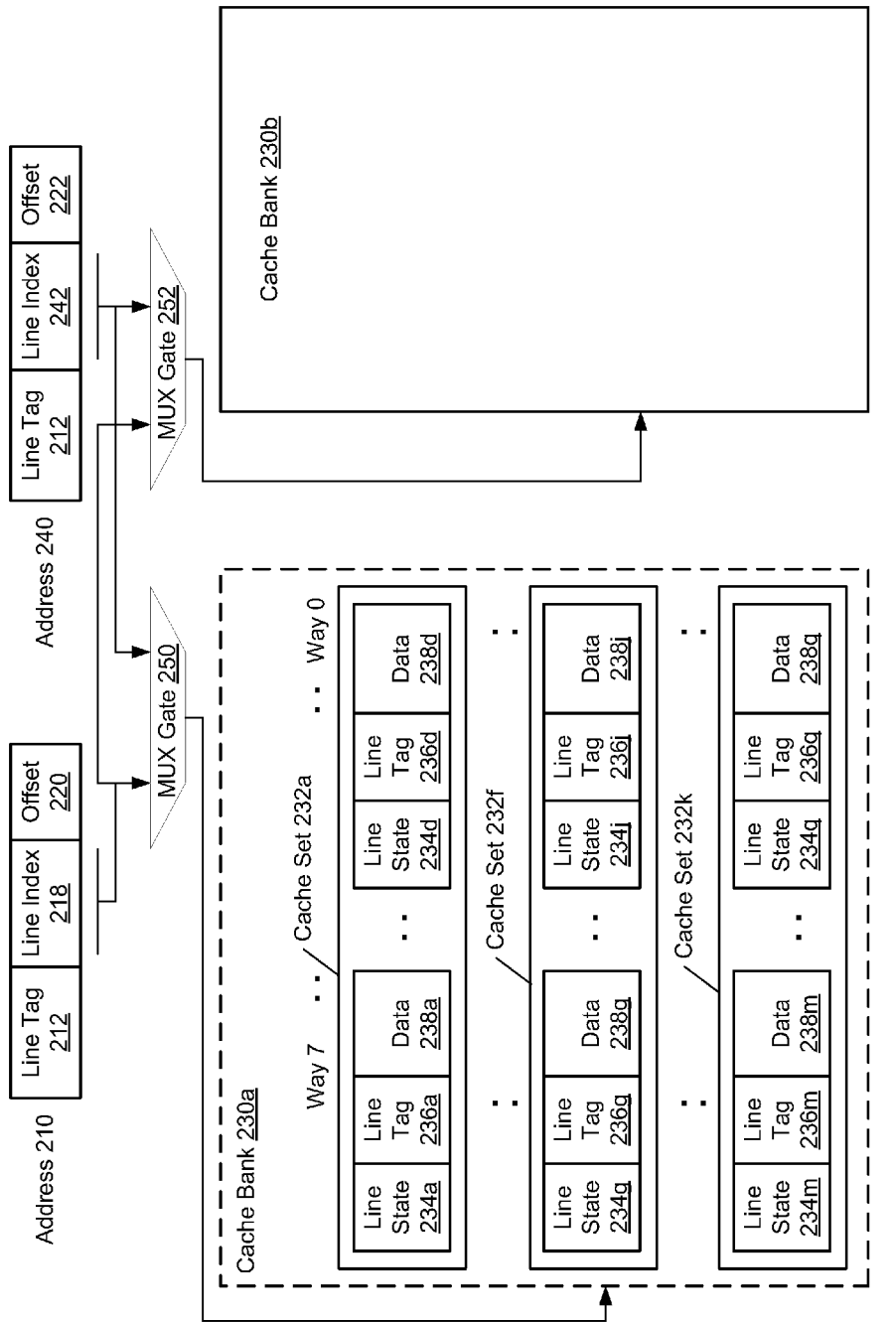
FIG. 2 is a generalized block diagram of one embodiment of banked data cache in which data are stored using a set-associative cache organization.

Data may be stored within the d-cache 26 in various manners. For example, a generalized block diagram in FIG. 2 illustrates one embodiment of a banked data cache in which data are stored using an 8-way set-associative cache organization. A different number of ways, such as 4-way, 16-way, or other, within the set-associative cache may be chosen. In one embodiment, the d-cache 26 may include two banks, such as bank 230*a* and 230*b*. One bank may be an even bank indexed by an even index portion of one of the two generated addresses 210 and 240. A second bank may be an odd bank indexed by an odd index portion of one of the two generated addresses 210 and 240.

One of the addresses 210 and 240 may be generated in response to executing a received memory access instruction. The generated address may be partitioned into a cache line tag 212, an index 218 and an offset 220. The offset may designate a number of bytes or words from a beginning of a cache line where a beginning of the requested data is located. A requested data size may be obtained during decode of the memory access instruction. In one example, the cache line index 218 has a value of 0x7777 DDDD 2264. This value is an even value and may be selected to access an even bank, such as bank 230*a*. The selection of which address to use for access may be performed by one of the multiplexer (mux) gates 250-252. This index value may be incremented to produce the cache line index 242 with a value of 0x7777 DDDD 2265. This value is an odd value and may be selected to access an odd bank, such as bank 230*b*. Again, the selection of which address to use for access may be performed by one of the multiplexer (mux) gates 250-252. A cache line hit may occur when the cache line tag value 212 matches a selected one of the stored cache line tags 236*a*-236*m* within a chosen set and a selected one of the cache line states 234*a*-234*m* indicates the selected cache line is a valid cache line.

The cache line offset 220 may have a value determined by the decoded memory access instruction. For example, the cache line offset 220 may have a value of 56, or 0x38, provided within the memory access instruction. The cache line offset 222 may have a value equal to the beginning of the second cache line. The number of bytes or words within the second cache line to be used to provide the requested data may be determined by calculating a difference between the requested data size and a size of the requested data size within the first cache line. For example, the cache line offset 222 may have a value of 0x00. For a requested data size of 16 bytes, the first 8 bytes of the requested data may be located in bytes 56 to 63 of a first cache line identified by the cache line index 218 with a value of 0x7777 DDDD 2264. The remaining 8 bytes of the requested data may be located in bytes 0 to 7 of a second cache line identified by the cache line index 242 with a value of 0x7777 DDDD 2265.

In one embodiment, each one of the data portions 238*a*-238*m* of a cache line stored within one of the banks 230*a*-230*b* is configured to store 64 bytes. Other sizes are possible and contemplated. Each of the 8 ways may also store cache line state information 234*a*-234*m*. This cache line state 334 may include at least one or more of the following: a valid bit, a cache line owner encoding that indicates the source which owns the corresponding cache line, Least Recently Used (LRU) eviction information used in association with a cache replacement algorithm employed by a cache controller, an indication that designates a cache coherency state such as modified, exclusive, owned, shared, invalid, or other. Other included state information is possible and contemplated.

The cache line tags 236*a*-236*m* may be used to determine which of the 8 cache lines are being accessed within a chosen one of the cache sets 232*a*-232*k*. In addition, each one of the offsets 220 and 222 of addresses 210 and 240 may be used to indicate a specific byte or word within a cache line. Although the cache line state information 234a-234m and cache line tags 236a-236m are shown as stored in contiguous bits with data portions 238a-238m within each cache way, in one embodiment, these values may be stored in a separate array, rather than in a same array with the data 238a-238m. In addition, the stored values may not be stored in contiguous bits and other storage arrangements are possible and contemplated.

Figure 3:
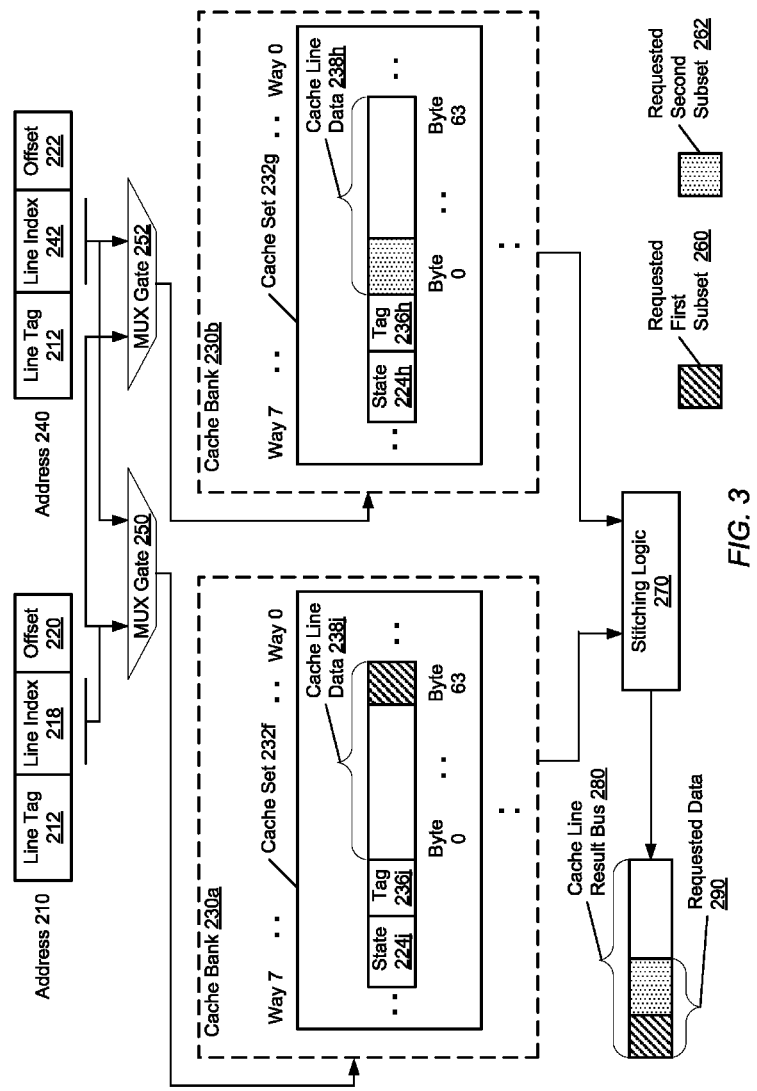
FIG. 3 is a generalized block diagram of one embodiment of another embodiment of banked data cache in which data are stored using a set-associative cache organization.

Turning now to FIG. 3, a generalized block diagram illustrates another embodiment of a banked data cache in which data are stored using an 8-way set-associative cache organization. Circuitry, logic and values used in FIG. 2 are numbered here identically. As described earlier, a particular cache set may be chosen in each of banks 230a-230b by the indexes 218 and 242. As shown in FIG. 3, cache sets 232f and 232h are selected in banks 230a and 230b, respectively. A memory access misalignment that crosses a cache line boundary occurs and it is detected. Therefore, after cache tag hits are detected in each of the banks 230a-230b, a first subset 260 of the requested data is read from a cache line in bank 230a. Simultaneously, a second subset 262 of the requested data is read from a cache line in bank 230b.

In one embodiment, during the simultaneous read operations of the banks 230a-230b, only the requested subsets of data are read, rather than the entire cache lines. An indication or flag may be used when a memory access misalignment is detected. This flag may be used to determine a selective read is to be performed for data from each of the cache line data portions 238j and 238h within banks 230a-230b. The stitching logic 270 may include control logic for selecting particular bytes within each of the cache lines within banks 230a-230b. For example, the decoded requested data size and generated offsets 220 and 222 may be used to locate the requested subsets 260 and 262. In addition, the stitching logic 270 may concatenate the subsets 260 and 262 according to a given format. The concatenation or other manner of joining the requested subsets together may be referred to as "stitching". The stitching logic 270 may place the subsets 260 and 262 on result data bus 280. In various embodiments, the result data bus 280 may have a size of one cache line. In this manner, portions of multiple cache lines may be conveyed on the bus 280 in a single bus transaction without performing additional read operations, or needing a flush of the pipeline or any micro-code execution despite a memory access misalignment. In other embodiments, bus widths of other sizes may be used.

Figure 4:
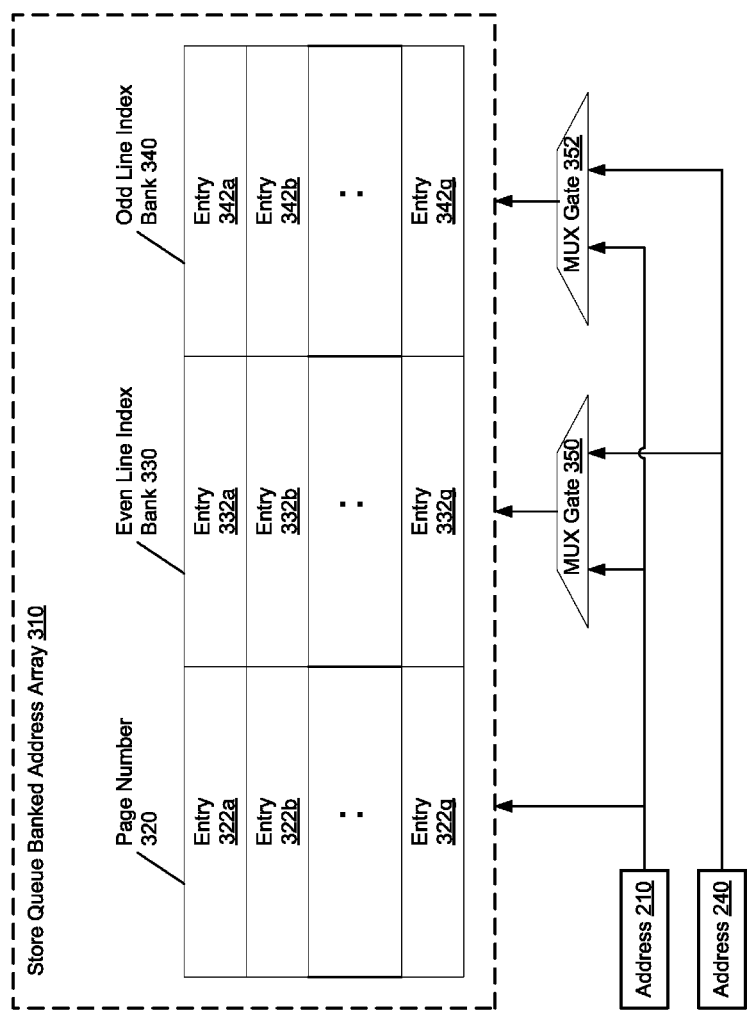
FIG. 4 is a generalized block diagram illustrating one embodiment of a banked store queue.

Referring now to FIG. 4, a generalized block diagram illustrating a banked store queue is shown. The banked store queue address array 310 may store issued but not-yet-committed store instructions. Each outstanding store instruction may have an entry in the banked store queue address array 310. The stored operations may also be micro-operations, or micro-ops, if processor 10 is able to divide instructions into two or more operations. The banked store queue address array 310 may be used in combination with a data array. The address array 310 may be used for read-after-write (RAW) hazard checking. Each load instruction may check the address array 310 for RAW hazards when they issue. Age information may be stored in the address array 310 or in a separate array that is also checked for RAW hazards.

The data array (not shown) holds the data of store instructions until these instructions commit. For a particular load instruction, when associated data is in a particular entry, which has valid data, bypass may occur immediately. Therefore, an access of the d-cache 26 may be cancelled. The data may be written when a store data operation is issued and is read both when the corresponding store instruction commits and when a RAW bypass occurs.

Similar to the banked d-cache 26, the banked store queue address array 310 may include two banks 330 and 340. In one embodiment, the bank 330 is an even bank and the bank 340 is an odd bank. The index portion of a generated address may be used to access one of these banks. Additionally, an incremented index based on the generated index portion may simultaneously access the other bank of these banks. The selection of which address to use for access may be performed by one of the multiplexer (mux) gates 350-352. The accessing examples with the index portions 218 and 242 described above regarding the banked d-cache 26 may be used in a similar manner with the banked store queue address array 310. Each index value 218 and 242 used to access the banked d-cache and the banked store queue 44 may have an associated valid bit, which may be asserted for regular store instructions and cache-line boundary crossing store instructions.

The address array 310 may include multiple entries, where each entry corresponds to a store instruction. The address array 310 may include three components including a page number portion 320, an even cache line index bank 330 and an odd cache line index bank 340. Each of the portions may include multiple entries 322a-322g, 332a-332g and 333a-333g, respectively. Entry 322a may store a page number corresponding to addresses stored in each of entries 332a and 333a. Similarly, entry 322g may store a page number corresponding to addresses stored in each of entries 332g and 333g. Intermittent entries may be set up in a same manner. In one embodiment, each of the entries 332a-332g and 333a-333g may store an entry number, status information, MESI protocol information, a thread identification (ID) number, and an address. Although the entries are shown in this particular order, other combinations are possible and additional fields may be included.

The address array 310 may have a content-addressable-memory (CAM) structure that is not banked, but allows simultaneous access to multiple entries. For example, the CAM structure may have at least two read word lines and two read ports for each entry. This CAM structure is typically implemented via dynamic circuit logic. Page-crossing store instructions have two different page numbers. In one embodiment, a separate smaller structure that stores a second page number may be used to avoid allocated on-die real estate for storing two page numbers per entry in the address array 310.

Figure 5:
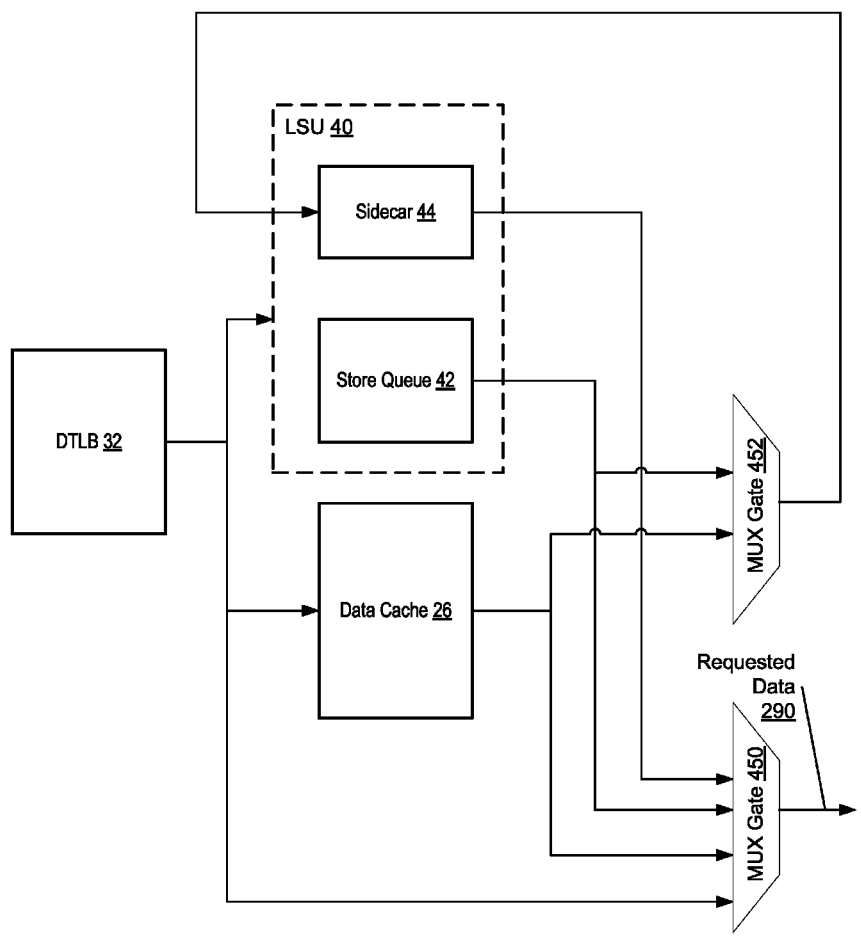
FIG. 5 is a generalized block diagram illustrating one embodiment of the use of a sidecar buffer mechanism.

Referring now to FIG. 5, a generalized block diagram of one embodiment of the use of a sidecar buffer mechanism is shown. As described above, when both cache lines of a misaligned load instruction are available in the d-cache 26 or the store queue 42, the load instruction is able to obtain its data without an additional load-to-use penalty. The additional load-to-use penalty may include additional read operations, micro-code instructions, generated micro-ops in the hardware and/or a flushed pipeline. This penalty may be avoided by the use of the simultaneous read operations for each bank within the d-cache 26 and the store queue 42 and described earlier.

During the execution of a misaligned load instruction, the DTLB 32 sends an address to each of the d-cache 26 and the store queue 42 within the LSU 40. If a hit occurs for each of the two cache lines corresponding to the misaligned memory access, then the requested data is simultaneously read out. This data read out is stitched together and then selected by mux gate 450 to be placed on the result data bus 290. Stitching logic (not shown) may be used to join different subsets from the two cache lines together to form the requested data. This stitching logic may be placed in front of the mux gate 450 or afterward. In a case that one of the two cache lines hits and one of the two cache lines misses after accessing the d-cache 26 and the store queue 42, the data within the cache line that hit may be selected by mux gate 452 and subsequently stored in the sidecar buffer 44. Also, a miss request may be sent to the memory subsystem for the data in the cache line that missed.

At a later time when the data corresponding to the miss cache line returns, this data may be stitched together with the data stored earlier in the sidecar buffer 44. The stitched result data may be selected by the mux gate 450 and placed on the result data bus 290. Stitching logic (not shown) may be used to join different subsets from the two cache lines together to form the requested data. This stitching logic may be placed in front of the mux gate 450 or afterward. At the same time, the DTLB 32 may access the d-cache 26, utilize a LRU algorithm and place the returned data in the d-cache 26 after an eviction of another cache line. In one embodiment, the misaligned load instruction may be replayed within the LSU 40 when the returned data arrives.

In a case that both of the two cache lines of a misaligned load instruction miss after accessing the d-cache 26 and the store queue 42, a miss request is sent for each cache line to the memory subsystem. The requested data is not stitched and placed on the result data bus 290 until both cache lines return as a result of the miss requests. In one embodiment, the sidecar buffer 44 has waiting entries and logic for handling the stitching of data when a cache line is returned by a serviced miss request. The sidecar buffer 44 has status information identifying missed cache lines to be used for stitching together requested data for a misaligned load instruction. In addition, the sidecar buffer 44 may allow the LSU 40 to handle misaligned loads and stores that are uncacheable and/or are directed to device memory space. In one embodiment, the LSU 40 may handle splitting and sequencing page-crossing store and load instructions in order to obtain the correct translation for both pages used.

As described above, a misaligned load instruction may be executed without incurring an additional load-to-use penalty that may otherwise be associated with misaligned loads. When a misaligned store instruction is detected, the DTLB 32 accesses with an associated address the store queue 42 within the LSU 40. Both the cache line index 218 and the incremented cache line index 242 are used. The write data is separated into two subsets according to the appropriate cache line to receive the subset. The subsets of data are simultaneously entered into the banked store queue 42. In one embodiment, the correct byte enables are set for the even and the odd indexes that are to be accessed. Therefore, a misaligned store instruction may occupy only one issue slot in the micro-architecture. An alternate solution to allow power reduction is to not support a single-issue slot for misaligned store instructions that cross a page boundary or to sequence them from the LSU 40 one behind the other. Therefore, support for concurrent translation lookups for two pages is not performed.

Figure 6:
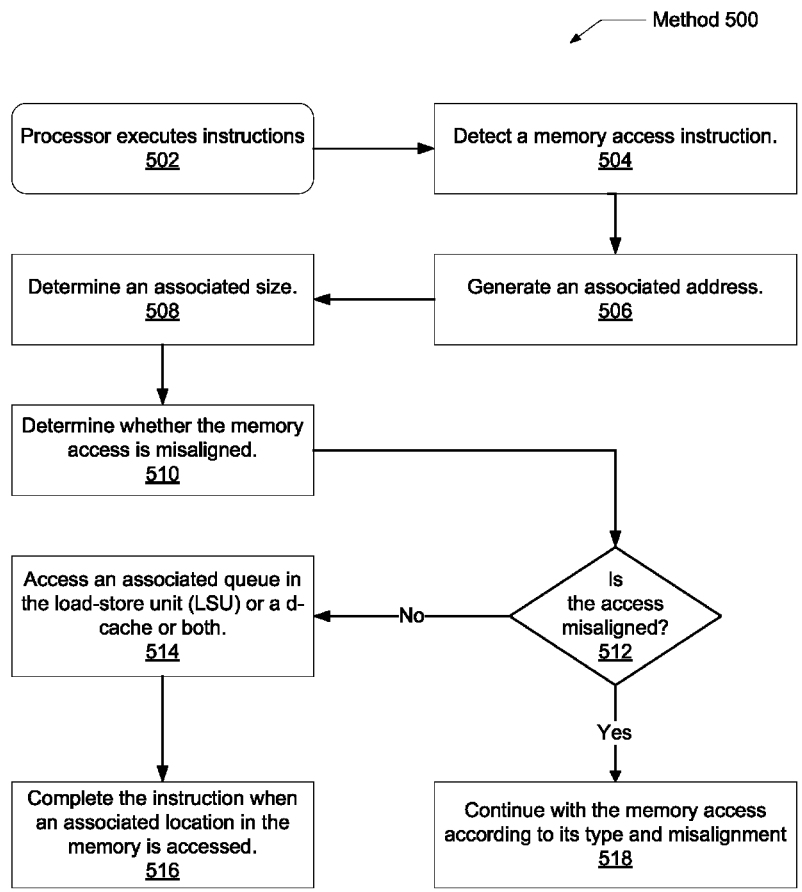
FIG. 6 is a generalized flow diagram illustrating one embodiment of a method for handling memory accesses in a processor.

Turning now to FIG. 6, one embodiment of a method 500 for handling memory accesses in a processor is shown. The components embodied in processor 10, the banked d-cache 26, the banked store queue 42 and the sidecar buffer may generally operate in accordance with method 500. For purposes of discussion, the steps in this embodiment and subsequent embodiments of methods described later are shown in sequential order. However, in other embodiments some steps may occur in a different order than shown, some steps may be performed concurrently, some steps may be combined with other steps, and some steps may be absent.

In block 502, the processor 10 may be executing instructions corresponding to one or more software applications. The processor 10 may fetch instructions concurrently for one or more threads. These fetched instructions are decoded and scheduled for execution. In block 504, the processor 10 detects a memory access instruction. In block 506, the processor 10 generates an associated address for the memory access instruction. The processor 10 may have a physically tagged or a virtually tagged d-cache 26 and store queue 42. In block 508, a data size for the requested data is detected by the decoded memory access instruction. The data size may be determined prior to the address.

In block 510, a determination is made whether the memory access is misaligned. Alignment detection may utilize both the least-significant bits of a generated address corresponding to the memory access instruction and the data size to be accessed. If (i) the size of the access data is less than a size of a cache line and (ii) the size of allocation from the offset within the generated address to the end of the cache line is not able to fit the requested data, then the memory access instruction is misaligned and crosses a cache line boundary.

If the memory access is not misaligned (conditional block 512), then in block 514, an access is made in an associated queue in the LSU 40 or the d-cache 26 or both. For example, a load buffer may have an entry allocated for a load instruction. At a later time, the store queue 42 may be accessed to find a potential RAW hazard and to bypass data from an older store instruction. The d-cache 26 may also be accessed. For a store instruction, the store queue 42 may be accessed and associated write data may be written into an allocated entry.

In block 516, the instruction is completed when an associated location in the memory is accessed. For example, requested data may be returned for one or more consumers or write data is sent to an associated memory location in the memory subsystem. If the memory access is misaligned (conditional block 512), then in block 518, the memory access is continued according to its type and given misalignment steps. These steps are further described in the methods below.

Figure 7:
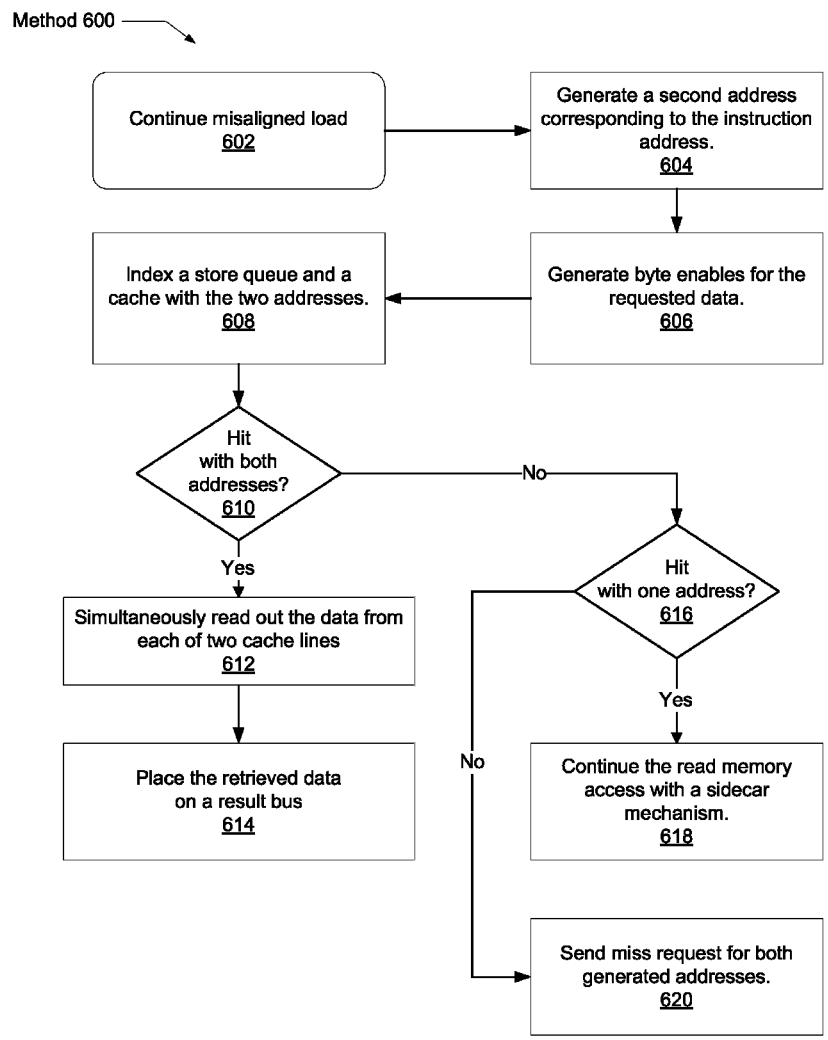
FIG. 7 is a generalized flow diagram illustrating one embodiment of a method for handling a misaligned load instruction in a processor.

Referring now to FIG. 7, one embodiment of a method 600 for handling a misaligned load instruction in a processor is shown. The components embodied in processor 10, the banked d-cache 26, the banked store queue 42 and the sidecar buffer may generally operate in accordance with method 600. For purposes of discussion, the steps in this embodiment and subsequent embodiments of methods described later are shown in sequential order. However, in other embodiments some steps may occur in a different order than shown, some steps may be performed concurrently, some steps may be combined with other steps, and some steps may be absent.

In block 602, the processor 10 continues processing a misaligned load instruction detected and started in method 500. In block 604, an incremented address is generated based on the instruction address. For example, the cache line index of the generated address may be incremented. Therefore, if the original index is even, then the incremented index is odd, and vice-versa. In block 606, one or more byte enables for the requested data may be generated. These byte enables may be based on the address offset and the requested data size. Referring again to FIG. 3, the subsets 260 and 262 that form the requested data show the bytes that may have the enables asserted. Alternatively, the offset and data size may be sufficient for accessing and stitching the subsets 260 and 262.

In block 608, both the banked store queue 42 and the banked d-cache 26 may be indexed with the two generated addresses. The two addresses may be output from the DTLB 32 and associated logic for creating an incremented address.

Alternatively, the incrementing logic for generating the second address may be located within each of the store queue 42 and the d-cache 26.

If a hit occurs for each of the two generated addresses (conditional block 610), then in block 612, each of the two cache lines corresponding to the two generated addresses may be simultaneously accessed. Additionally, data may be selected from the store queue as well (even if there is a hit in the cache), given the store queue may hold data that is more current. One or more bytes of identified requested data may be read from each cache line. In one embodiment, the particular requested bytes may be identified by an offset in the address and the data size. Referring again to FIG. 3, a first subset 260 in a first cache line may be selected by identifying a first location at a distance from a beginning of the first cache line equal to an offset within the generated address corresponding to the first cache line. Then data from the first location to the end of the first cache line may be selected as the first subset. A second subset 262 in a second cache line may be selected by identifying a second location at a distance from a beginning of the second cache line equal to a difference between the requested data size and a size of the first subset. Then data from the beginning of the second cache line to the second location may be selected as the second subset. Alternatively, byte enables may have been generated from this information and conveyed to stitching and selection logic.

In block 614, stitching logic may join the first subset and the second subset together in a given format. The joined data may be placed on a result data bus with a size equal to a single cache line. Therefore, a wider data bus is not used for a simultaneous access of two cache lines.

If a hit occurs for one of the two generated addresses (conditional block 610), then in block 618, the misaligned load instruction is processed with a sidecar buffer mechanism. The steps for this mechanism are further described below in method 700. If no hit occurs for each of the two generated addresses (conditional block 610), then in block 620, a miss request is sent for each of the generated addresses to the memory subsystem.

Figure 8:
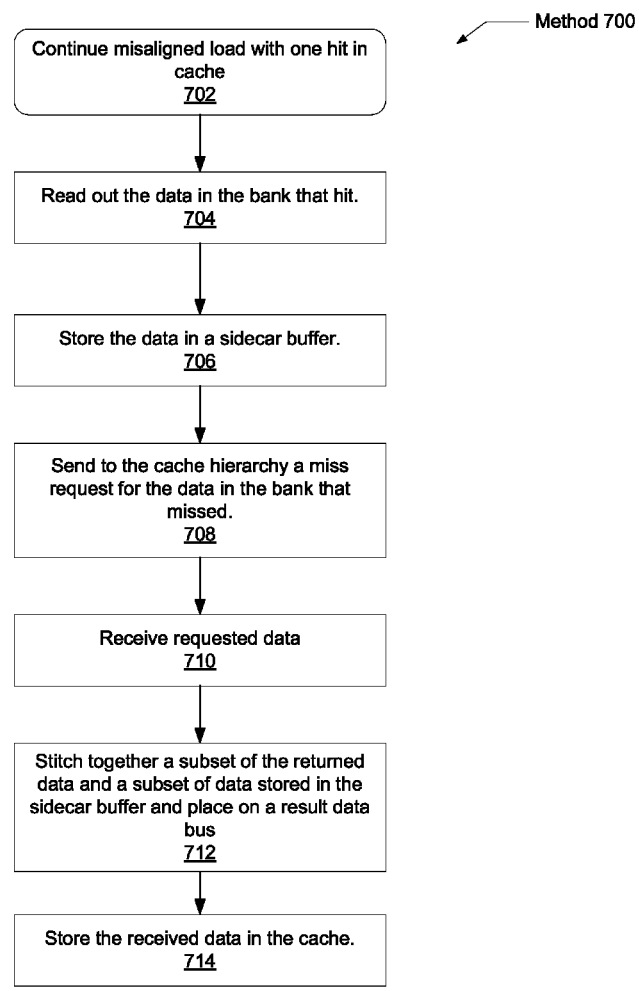
FIG. 8 is a generalized flow diagram illustrating one embodiment of a method for handling a misaligned load instruction with a sidecar buffer mechanism in a processor.

Turning now to FIG. 8, one embodiment of a method 700 for handling a misaligned load instruction with a sidecar buffer mechanism in a processor is shown. Similar to methods 500 and 600, the components embodied in processor 10, the banked d-cache 26, the banked store queue 42 and the sidecar buffer 44 may generally operate in accordance with method 700. For purposes of discussion, the steps in this embodiment and subsequent embodiments of methods described later are shown in sequential order. However, in other embodiments some steps may occur in a different order than shown, some steps may be performed concurrently, some steps may be combined with other steps, and some steps may be absent.

In block 702, the processor 10 continues processing a misaligned load instruction with one hit and one miss in the d-cache 26 and the store queue 42 as detected in method 600. In block 704, data in the cache line that resulted in a hit is read out. This data is stored in the sidecar buffer 44 in block 706. An indication of the cache line that resulted in a miss may be stored with this data. In block 708, a miss request may be sent to the memory subsystem for the data in the cache line that resulted in a miss.

In block 710, the miss request may be serviced. The data in the cache line that earlier caused a miss may be returned. In block 712, the sidecar buffer 44 may be accessed when the previously missed cache line returns. Detection is made that the returned cache line is part of a misaligned load instruction. The first subset within a first cache line may be identified and stitched together with an identified second subset in a second cache line. The joined data may be placed on a result data bus with a size equal to a single cache line. Therefore, a wider data bus is not used for a simultaneous access of two cache lines. In block 714, the returned cache line may be stored in the d-cache 26.

Figure 9:
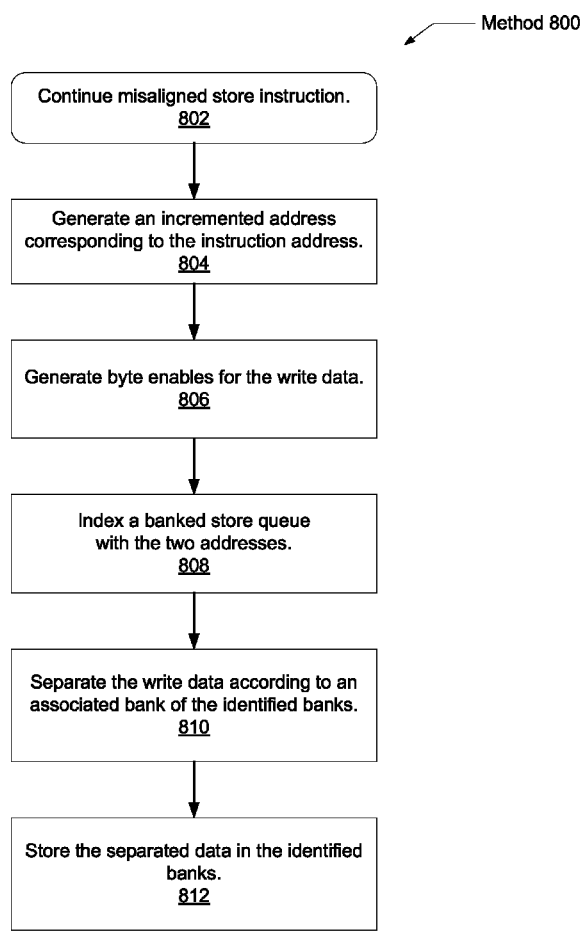
FIG. 9 is a generalized flow diagram illustrating one embodiment of a method for handling a misaligned store instruction in a processor.

Referring now to FIG. 9, one embodiment of a method 800 for handling a misaligned store instruction in a processor is shown. Similar to methods 500-700, the components embodied in processor 10, the banked d-cache 26, and the banked store queue 42 may generally operate in accordance with method 800. For purposes of discussion, the steps in this embodiment and subsequent embodiments of methods described later are shown in sequential order. However, in other embodiments some steps may occur in a different order than shown, some steps may be performed concurrently, some steps may be combined with other steps, and some steps may be absent.

In block 802, the processor 10 continues processing a misaligned store instruction detected and started in method 500. In block 804, an incremented address is generated based on the instruction address. For example, the cache line index of the generated address may be incremented. Therefore, if the original index is even, then the incremented index is odd, and vice-versa. In block 806, one or more byte enables for the associated write data may be generated. These byte enables may be based on the address offset and the write data size.

In block 808, the banked store queue 42 may be indexed with the two generated addresses. The two addresses may be output from the DTLB 32 and associated logic for creating an incremented address. Alternatively, the incrementing logic for generating the second address may be located within the store queue 42.

In block 810, the write data may be separated into a first subset and a second subset according to an associated bank of the identified banks. A similar identification process for the subsets as described above in step 612 for a misaligned load instruction may be used for determining which bytes to modify in each of the first and the second cache line. In block 812, the data in the first subset and the second subset may be simultaneously stored in associated entries in the store queue 42.

In addition to the above, program instructions stored on a computer readable storage medium may comprise behavioral-level description or register-transfer level (RTL) descriptions of the hardware functionality corresponding to the above described embodiments in a high level programming language such as C, or a design language (HDL) such as Verilog, VHDL, or database format such as GDS II stream format (GDSII). In various embodiments, such instructions may be utilized by various tools which may synthesize the description to produce a netlist comprising a list of gates from a synthesis library. Such a netlist may represent the functionality of the hardware comprising the system and may be further used in various semiconductor fabrication processes to produce a circuits corresponding to the system. Alternatively, the instructions on the computer accessible storage medium may be the netlist (with or without the synthesis library) or the data set, as desired. Additionally, such instructions may also be utilized for purposes of emulation.

Although the embodiments above have been described in considerable detail, numerous variations and modifications will become apparent to those skilled in the art once the above disclosure is fully appreciated. It is intended that the following claims be interpreted to embrace all such variations and modifications.

What is claimed is:

1. A method comprising:
   detecting a memory access corresponding to a first cache line;
   generating a first address corresponding to the memory access;
   in response to determining the memory access is a misaligned read operation, based at least in part on the first address and a requested data size:
      determining a first subset of data corresponding to the memory access corresponds to the first cache line and a second subset of data corresponding to the memory access corresponds to a second cache line;
      generating a second address corresponding to the second cache line;
      in response to determining each of the first cache line and the second cache line is in the cache, conveying both the first subset of data and the second subset of data from the cache;
      in response to determining the first cache line is in the cache and the second cache line is not in the cache:
         sending a request for the second cache line to a memory subsystem;
         receiving the second cache line from the memory subsystem;
         in response to receiving the second cache line from the memory subsystem, storing the second cache line in the cache and not in a sidecar buffer of a load store unit (LSU);
         retrieving the second subset of data from the second cache line; and
         placing both the first subset of data and the second subset of data on a data bus simultaneously.

2. The method as recited in claim 1, further comprising placing the first subset and the second subset in contiguous locations on the data bus to be conveyed as a single response to the read operation, wherein the data bus has a width of a single cache line.

3. The method as recited in claim 1, wherein in further response to determining the first cache line is available and the second cache line is unavailable in the cache, the method further comprises:
   storing the first subset in the sidecar buffer; and
   in response to receiving the second cache line from the memory subsystem:
      retrieving the first subset from the sidecar buffer; and
      retrieving the second subset from the second cache line.

4. The method as recited in claim 3, wherein for a given read operation, the sidecar buffer is only accessed after the cache is accessed responsive to (i) determining the given read operation is misaligned and (ii) either determining only one of two cache lines corresponding to the given read operation is available in the cache or receiving a cache line from the memory subsystem for the given read operation.

5. The method as recited in claim 1, wherein determining said memory access is a misaligned read operation comprises determining read data corresponding to the read operation crosses a cache line boundary.

6. The method as recited in claim 1, wherein in response to receiving the second cache line from the memory subsystem, the method further comprises replaying the misaligned read operation.

7. The method as recited in claim 1, wherein in response to determining the memory access is a misaligned write operation, the method further comprises:
   separating write data corresponding to the write operation into a first subset and a second subset; and
   simultaneously storing both the first subset and the second subset in association with different cache lines.

8. An apparatus comprising:
   a fetch unit configured to fetch instructions;
   a decode unit coupled to the fetch unit configured to decode fetched instructions; and
   an execution core configured to execute memory access instructions, wherein the execution core comprises a load-store unit (LSU) including a sidecar buffer and a cache;
   wherein the execution core is configured to:
      detect a memory access corresponding to a first cache line;
      generate a first address corresponding to the memory access;
      in response to determining the memory access is a misaligned read operation based at least in part on the first address and a requested data size:
         determine a first subset of data corresponding to the memory access corresponds to the first cache line and a second subset of data corresponding to the memory access corresponds to a second cache line;
         generate a second address corresponding to the second cache line;
         in response to determining each of the first cache line and the second cache line is in the cache, convey both the first subset of data and the second subset of data from the cache;
         in response to determining the first cache line is in the cache and the second cache line is not in the cache:
            send a request for the second cache line to a memory subsystem; and
            receive the second cache line from the memory subsystem;
            in response to receiving the second cache line from the memory subsystem, store the second cache line in the cache and not in the sidecar buffer;
            retrieve the second subset of data from the second cache line; and
            place both the first subset of data and the second subset of data on a data bus simultaneously.

9. The apparatus as recited in claim 8, wherein the execution core is further configured to generate byte enables used to select the first subset and the second subset.

10. The apparatus as recited in claim 9, wherein the execution core is further configured to place the first subset and the second subset in contiguous locations on the data bus to be conveyed as a single response to the read operation, wherein the data bus has a width of a single cache line.

11. The apparatus as recited in claim 9, wherein in further response to determining simultaneously the first cache line is available and the second cache line is unavailable, the execution core is further configured to:
    store the first subset in the sidecar buffer; and
    in response to receiving the second cache line from the memory subsystem:
       retrieve the first subset from the sidecar buffer; and
       retrieve the second subset from the second cache line.

12. The apparatus as recited in claim 11, wherein for a given read operation, the sidecar buffer is only accessed after the cache is accessed responsive to (i) determining the given read operation is misaligned and (ii) either determining only one of two cache lines corresponding to the given read operation is available in the cache or receiving a cache line from the memory subsystem for the given read operation.

13. The apparatus as recited in claim 8, wherein determining said memory access is a misaligned read operation comprises the execution core determining read data corresponding to the read operation crosses a cache line boundary.

14. The apparatus as recited in claim 8, wherein in response to receiving the second cache line from the memory subsystem, the method further comprises replaying the misaligned read operation.

15. The apparatus as recited in claim 8, wherein in response to determining the memory access is a misaligned write operation, the execution core is further configured to:
separate write data corresponding to the write operation into a first subset and a second subset; and
simultaneously store both the first subset and the second subset in association with different cache lines.

16. An apparatus comprising:
a cache; and
a load store unit (LSU) including a sidecar buffer, wherein the LSU is configured to:
detect a memory access corresponding to a first cache line;
generate a first address corresponding to the memory access;
in response to determining the memory access is a misaligned read operation based at least in part on the address and a requested data size:
determine a first subset of data corresponding to the memory access corresponds to the first cache line and a second subset of data corresponding to the memory access corresponds to a second cache line;
generate a second address corresponding to the second cache line;
in response to determining each of the first cache line and the second cache line is in the cache, select a first subset of data within the first cache line and a second subset of data within the second cache line;
in response to determining the first cache line is in the cache and the second cache line is not in the cache:
send a request for the second cache line to a memory subsystem;
receive the second cache line from the memory subsystem;
in response to receiving the second cache line from the memory subsystem, store the second cache line in the cache and not in the sidecar buffer;
retrieve the second subset of data from the second cache line; and
return both the first subset and the second subset simultaneously in a single response to the memory access.

17. The apparatus as recited in claim 16, wherein the LSU is configured to determine said memory access is a misaligned access in response to determining read data corresponding to the memory access crosses a cache line boundary.

18. The apparatus as recited in claim 17, wherein the LSU is configured to return the first subset and second subset via a data bus that has a width of a single cache line.

19. A non-transitory computer readable storage medium storing program instructions, wherein the program instructions are executable to:
detect a memory access to a first cache line within a cache;
generate a first address corresponding to the memory access;
in response to determining the memory access is a misaligned read operation based at least in part on the address and a requested data size:
determine a first subset of data corresponding to the memory access corresponds to the first cache line and a second subset of data corresponding to the memory access corresponds to a second cache line;
generate a second address corresponding to the second cache line;
in response to determining each of the first cache line and the second cache line is in the cache, select simultaneously both a first subset within the first cache line and a second subset within the second cache line;
in response to determining the first cache line is in the cache and the second cache line is not in the cache:
send a request for the second cache line to a memory subsystem;
receive the second cache line from the memory subsystem;
in response to receiving the second cache line from the memory subsystem, store the second cache line in the cache and not in a sidecar buffer of a load store unit (LSU);
retrieve the second subset of data from the second cache line; and
place both the first subset of data and the second subset of data on a data bus simultaneously.

\* \* \* \* \*